United States Patent [19]
Lataix

[11] Patent Number: 5,390,822
[45] Date of Patent: Feb. 21, 1995

[54] PACKAGING VIAL FOR A LIQUID PRODUCT IN PARTICULAR MEDICINAL OR COSMETIC

[75] Inventor: Gilbert Lataix, Clermont-Ferrand, France

[73] Assignee: Merck & Co., Inc., Rahway, N.J.

[21] Appl. No.: 97,635

[22] Filed: Jul. 26, 1993

[51] Int. Cl.$^6$ ............................................. B67D 5/24
[52] U.S. Cl. ................................. 222/30; 222/185; 222/385; 222/494
[58] Field of Search ............... 222/181, 185, 206–214, 222/321, 783, 385, 504, 509, 494, 30, 36

[56] References Cited

U.S. PATENT DOCUMENTS

| | | | |
|---|---|---|---|
| 3,409,184 | 11/1968 | Stengle, Jr. | 222/321 |
| 4,757,922 | 7/1988 | Landecker | 222/321 X |
| 4,792,334 | 12/1988 | Py . | |
| 4,946,452 | 8/1990 | Py . | |
| 4,949,877 | 8/1990 | Hanna et al. | 222/185 X |
| 4,964,544 | 10/1990 | Hanna et al. | 222/321 X |
| 5,105,992 | 4/1992 | Fender et al. | 222/185 |
| 5,165,577 | 11/1992 | Ophardt | 222/181 |
| 5,211,314 | 5/1993 | Burrows | 222/185 |
| 5,277,334 | 6/1994 | Malinconico | 222/36 |
| 5,282,552 | 2/1994 | Ophardt | 222/181 |

FOREIGN PATENT DOCUMENTS

0437953A1 7/1991 European Pat. Off. .

*Primary Examiner*—Andres Kashnikow
*Assistant Examiner*—Kenneth DeRosa
*Attorney, Agent, or Firm*—Hesna J. Pfeiffer; Mark R. Daniel

[57] ABSTRACT

Packaging vial for a liquid product in particular medicinal or cosmetic, manufacturing process and device for use of this vial. The vial includes a flexible casing (1), coupled to a rigid support (2), the casing (1) consisting of a pocket (10) with thin and distortable walls, containing the product and free from air, as well as a tubular nozzle (11) for dispensing the product, to which is coupled the pocket (10), the vial including furthermore a pump for dosing and delivering the product, said pump containing a fixed body inserted into the nozzle (11) and a moveable actuating member which is located inside the casing, but which can be moved from the outside of the latter thanks to the distortable character of its wall which, proximate the actuating member, has the shape of a bellows.

5 Claims, 8 Drawing Sheets

PACKAGING VIAL FOR A LIQUID PRODUCT IN PARTICULAR MEDICINAL OR COSMETIC

BACKGROUND AND SUMMARY OF THE INVENTION

The present invention is directed to a packaging vial for a liquid product, in particular medicinal or cosmetic, for example eye lotion which is designed to be instilled into the eye of a person. The present invention is also directed to the manufacturing process of this vial.

For the purposes of this description and claims, by "liquid product" is meant a liquid or pasty substance, likely to conform to the shape of its container, and to be expelled therefrom in the form of a stream, which is continuous or composed of individual drops.

In certain therapeutic treatments, it is necessary to periodically dispense a dose of a liquid medicament contained in a vial, to inject or deposit it in a precise place of the organism of the patient.

Thus, for example, for treating glaucoma, the patient must instil regularly—in general once in the morning and once in the evening—a determined dose of eye lotion into each eye.

In many applications, it is important that the delivered dose has a well determined volume. The supply of a too small quantity may affect the effectiveness of the treatment. The supply of a too large quantity not only wastes product, but furthermore may cause side effects. This is how, to return to eye treatment, the excess volume of eye lotion (not absorbed by the surface of the eye) may pass, via the tear duct, into the mouth, then into the esophagus and stomach of the patient. Yet, the ingestion of certain eye lotions can sometimes present a danger, particularly if they contain beta-blocking agents.

It is thus important to be able to deliver the exact dose of the product required by the patient.

It is already common practice to package liquid medicaments in vials with flexible walls. In this case, the product dose is dispensed by pressing the wall, either manually, or by employing an appropriate apparatus.

This is how, for example, specification EP-A-0 437 953, describes an eye lotion instillation apparatus whose embodiment represented in FIGS. 1 through 4 includes a housing receiving a vial filled with eye lotion. The vial has the general shape of a bottle having a semi-rigid cylindrical body, with an elastically distortable wall, as well as a nozzle pierced with a product outlet orifice. The apparatus is shaped so that it can be applied against the eyeball and it is equipped with a moveable member, for example a rotating roller, capable of pushing the eyelid back to the cul-de-sac level during instillation. The housing is equipped with an articulated lever outfitted with a projection coming into contact with the wall of the vial body. The end of this lever is engaged with the roller, in an offset manner. To use the apparatus, the patient holds it in one hand, and after having correctly positioned it against the eyeball, presses with his fingers on the lever so as to simultaneously, push back the eyelid and expose the cul-de-sac (by rotation of the roller) and make a drop of the product come out (by distortion of the vial wall).

This type of device is not entirely satisfactory since the quantity of eye lotion expelled from the vial is not precise. It depends directly on the dimensions of the outlet orifice, as well as on the pressure exerted by the user on the housing. The result is thus linked to the strength and skill of the patient. This is a genuine problem since this type of apparatus is often intended for use by elderly people, not always acting with the skill required.

Another disadvantage of this type of device comes from the fact that after a certain dose of the product has been dispensed, the wall of the vial elastically takes back its initial shape, sucking therein a volume of air equal to that of the dose of the product that was dispensed. Thus, the vial progressively fills up with air, as the volume of the product diminishes. This mass of air, harmful for certain products, is a source of contamination that should be avoided.

In another embodiment of the vial, which is represented in FIG. 34 of the above mentioned specification EP-A-0 437 953, the valve for dosing and dispensing eye lotion is integrated into the vial. The latter includes a first rigid hollow body, containing the product, capable of telescopically sliding into a second hollow body, which is also rigid. The latter is firmly attached to a valve stem which is pierced with a central channel and bears a shoulder located inside the inner hollow body and capable of fitting into a cavity formed in the bottom wall thereof. The unit comprised of the two telescopic bodies and of the valve acts as a pump. By thrusting the inner body into the outer body, the shoulder is made to come out of the cavity, which allows the product to enter therein. First, the reverse movement, caused by a spring placed between the two hollow bodies, traps a certain volume of liquid in the cavity, and it then drives it therefrom under pressure. This volume is then expelled through the channel cut in the valve stem, coming out of the vial in the form of drops through a small valve provided at the end of the outer hollow body.

This vial, which is designed for use with a special instilling apparatus, also described in this specification, is in principle adapted to dispensing properly measured successive doses of the product, doses whose volume corresponds to that of the cavity.

Furthermore, the inner body is sealed by a cap which is capable of sliding therein like a piston in a cylinder, as the volume of the liquid diminishes, which compensates for this reduction in volume and prevents air from entering the vial.

This solution is not acceptable for the packaging of most cosmetic or pharmaceutical products because the piston/cylinder contacting walls, which define a sliding seal, enable the propagation of external bacteria toward the inside of the vial. The sliding seal is also a source of leakages.

Furthermore, the structure of such a vial, which requires a high number of parts, is not adapted to the manufacturing on a large or very large scale.

The main object of the present invention is to avoid these various disadvantages by proposing a vial of the type mentioned above, which, while allowing the delivery of successive doses of liquid product in the form of a well defined and exact volume, may be mass produced at a large, even very large scale, with a very low cost price, this in perfect conditions of hygiene, during the vial manufacturing process as well as when it is being filled, its later storage and its final use by the patient.

Another object of this invention is to plan for means of informing the user of the fact that the number of doses for which the vial is assigned has been reached, even which renders the vial unusable at this point.

Another object of this invention is to plan for means which accomplish the expulsion of the product in the form of a stream or drops according to a well defined space direction, and from a certain angle in relation to the general axis of the vial. This is particularly interesting for the installation of eye lotion since, in this case, the drops must preferably be accurately projected into the cul-de-sac located at the base and in an angle of the eye.

This invention is also directed to a vial manufacturing process which is especially economical and satisfactory regarding hygiene and quality of the finished product, this product being adapted to be mass produced at a large or even very large scale.

These various objects are fulfilled, according to this invention, thanks to the fact that the packaging vial includes a flexible casing attached to a rigid support, this casing comprising a pocket with thin and distortable walls, containing the product and free of air, as well as a tubular nozzle for delivering the product, to which is connected the pocket, and that the pump is a part of the vial, this pump including a fixed body inserted into the nozzle and a moveable actuating member which is located inside the casing, but which can be displaced from the outside of the latter, given the distortable character of its wall close to the actuating member.

Furthermore, according to a certain number of additional non-limiting characteristics:

- the nozzle is sealed by an easily tearaway element, for example divisible;
- said rigid support includes a cartridge made out of plastic material, provided with a means for retaining the nozzle and the pocket centering members;
- the means for retaining the nozzle is a bracket set at a right angle in relation to the plane of said cartridge and pierced with an aperture in which the nozzle is ratchetably fixed and then locked;
- the centering members of the pocket consist of a pair of legs set at a right angle in relation to the plane of said cartridge, between which the pocket is made fit;
- at least one of said legs bears an informative mark in relation to the product or to the characteristics of the vial;
- the pocket has an elongated shape of which the major axis substantially extends the axis of the tubular nozzle, the bottom of this pocket, which is located at the opposite end of the nozzle, being closed by soldering;
- the vial is provided with means for counting the number of doses delivered, which are borne by the rigid support;
- the counting means include two free-rotating gears located near one another of which the first is designed to turn a fraction of a turn each time that a dose of the product is delivered and it is designed to turn the second gear a fraction of a turn, by using an actuating leg, each time it goes completely around;
- one of the teeth of the second gear is shaped in such a way that it prohibits movement to be continued after a complete turn of this second gear;
- the pump includes a variable volume chamber and is arranged so that the movement of said actuating member in one direction accomplishes sucking up of the product in the pocket into the chamber, while its movement in the other direction accomplishes a backward flow of a calibrated dose of the product therefrom, to the outside of the casing;
- the pump body is pierced with a channel which from the uphill side (towards the inside of the casing) comes out in said chamber and from the downhill side (towards the outside) comes out opposite the inner wall of the end portion of the nozzle, this wall applying itself intimately against the outer wall of the body and presenting an easily distortable zone, the pressure of the product during backward flow being sufficient to temporarily spread said easily distortable zone apart from the body of the pump and allow the product to be ejected therefrom;
- the easily distortable zone extends peripherally over a limited portion, while the rest of the periphery of the wall of the nozzle is relatively firm in this area, so that the ejection of the product takes place according to a determined space orientation;
- the easily distortable zone is obtained by the presence of a cavity cut in the wall of the nozzle;
- On the uphill side, the pump body shows a truncated cone-like free end, so that the ejection of the product takes place according to an acute angle in relation to the axis of the nozzle;
- the nozzle has a general shape of revolution, while the pump body also has at least one portion with the general shape of a revolution fitted into the nozzle, coaxially with the latter, this portion showing an annular shoulder providing its connection in axial direction with the wall of the nozzle;
- the actuating member of the pump is moveable in translation according to the axis of the nozzle and of the pump body, and has an annular base providing its connection in axial direction with the wall of the nozzle near the connecting zone of the latter with the pocket, while, in its portion separating the shoulder from the base, the wall of the nozzle forms an axially distortable bellow;
- the actuating member of the pump is moveable in translation according to an axis perpendicular to the axis common to the nozzle and to the portion of the pump body which has a shape of a revolution;
- the actuating member of the pump is situated inside the pocket, facing a zone of its wall which is coupled to the rest of the pocket wall by a bellows which is transversely distortable in relation to said common axis.
- the pump body shows a pan which is set at a right angle in relation to the portion fitted into the nozzle and which serves to guide the actuating member in translation;
- the actuating member has the general shape of a socket which shows a cylindrical part with a closed bottom forming a cylinder, while said part set at a right angle in relation to the pump body includes a tubular cylindrical sleeve forming a piston, which fits into this cylindrical portion;
- the inside of the sleeve and the inside of the cylindrical part define said variable volume chamber;
- the vial includes a spring accommodated in the pocket which stresses the actuating member in the direction of an extension of the bellows and of a reduction of the volume of said variable volume chamber;
- the easily tearaway sealing element is obtained by crushing the end portion of a tubular part made of relatively rigid material which is molded on the end of the nozzle, this element being separated from the rest of the part by a divisible zone;

The manufacturing process of a packaging vial such as that which has just been presented above, is remarkable in that it includes the following steps:
  a) The flexible casing out of synthetic material, the latter having its bottom open on one hand and on the other hand a strengthening piece out of plastic material whose said rigid support is a constituent which can be easily separated therefrom are made through molding;
  b) the casing is coupled to said rigid support;
  c) the pump is introduced inside the pocket through the open bottom, and the fixed body is inserted therein into the nozzle;
  d) the end of the nozzle is sealed by soldering;
  e) the pocket is filled with the product;
  f) the bottom of the pocket is sealed by soldering;
  g) certain constituent elements of the strengthening piece are detached from said rigid support, said elements having been useful for the transport, guiding and placing of the pump.

Furthermore, according to a certain number of additional advantageous but non-limiting characteristics of the process:
  when the vial contains a rigid support provided with counting means, these means are accomplished through molding, at the same time as the rigid support;
  during step (c), the casing is pneumatically inflated so as to facilitate insertion of the pump body into the nozzle, the latter being in an expanded state, said operation being carded out by using the rigid part of the support as a sill for the inflating head;
  at the end of step (c), the behavior of the pump and of the nozzle is tested by internally pressurizing the casing;
  after step (d), the casing—pump—strengthening piece group is temporarily packaged in a sealed film, then sterilized;
  steps (e) and (f) are carded out in a vacuum and in a sterile environment;
  the strengthening piece has the general shape of a rectangular parallelepiped delimited by two substantially rectangular cartridges set opposite one another, and of which one is a constituent of said rigid support, these cartridges being coupled two by two by their small sides, employing divisible fasteners, to frame-shaped elements, the whole unit forming a housing which can receive and retain the casing;
  one of the frame-shaped elements is adapted to support the outer side of the open bottom edge of the pocket, when internal pressure is applied thereon, during or at the end of step (c);
  a group of strengthening pieces juxtaposed and grouped together is simultaneously molded, so that the two cartridges delimiting the rectangular parallelepiped of a strengthening piece consist in its own rigid support for one of the two cartridges, and in the rigid support of an adjacent piece for the other cartridge;

Other characteristics and advantages of this invention shall appear in the description which shall now be made with reference to the appended drawings.

BRIEF DESCRIPTION OF THE DRAWINGS

FIG. 4 is an exploded perspective view of the pump the vial of FIG. 1 is equipped with.

FIG. 5 is an axial cross sectional view of the nozzle of the vial, this view being intended to show how the pump is inserted into the nozzle.

FIG. 6 is a perspective view of the flexible casing obtained by molding, at the very beginning of manufacture of the vial.

FIGS. 10 to 14 illustrate the manufacturing process of the vial.

DETAILED DESCRIPTION OF THE INVENTION

Figure 1:
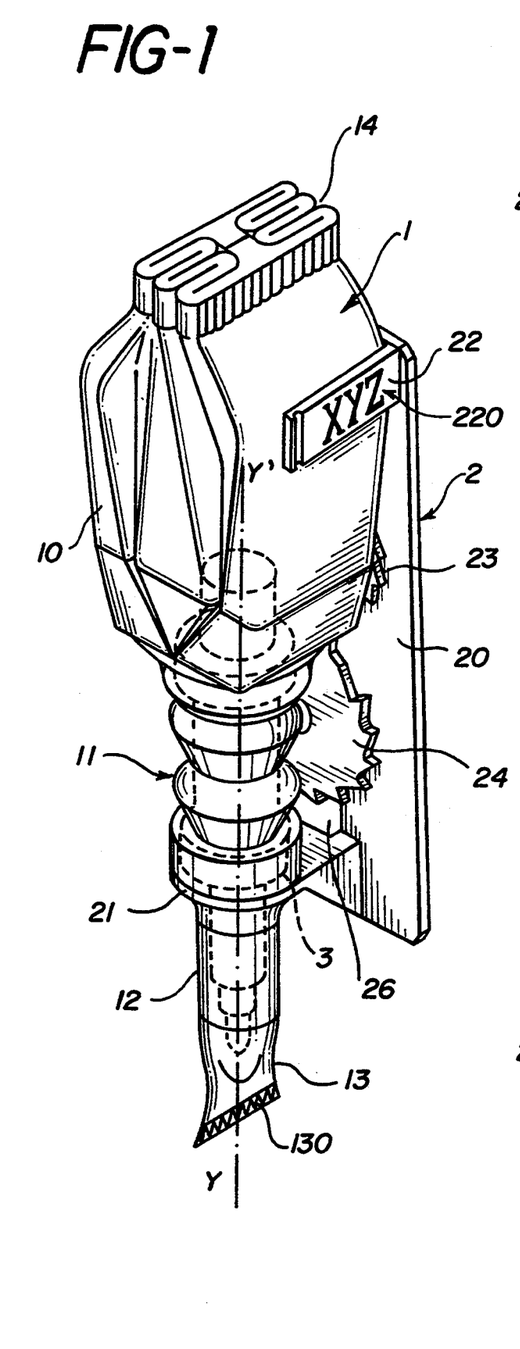
FIG. 1 is a perspective view of a first possible embodiment of the invention.

The vial represented in FIG. 1 essentially includes a flexible casing 1, a rigid support 2, and a pump 3.

These three elements are made of synthetic material.

The material forming casing 1 is a very flexible and distortable elastomeric material (synthetic rubber). The material in which support 2 and pump 3 are manufactured is a more rigid plastic material, for example polystyrene and polyethylene respectively.

Casing 1 is made up of a pocket 10 containing the product and of a tubular nozzle 11 which serves to deliver the product. These two parts are made all in one piece. Pocket 10 has a thin wall, which gives it a lot of flexibility. Pocket 10 has an elongated shape, and one of its ends, forming its bottom, forms a bellows 14 sealed by crushing and soldering, for example heat welding. In its central part, the pocket has an oval or rectangular section with rounded corners. Of course, this central zone is coupled to bottom 14 by pleats due to the configuration of the bellows-like sealing. At the other end, nozzle 11 has a shape of a revolution, and the Y–Y'axis of the nozzle corresponds to the major axis of the elongated pocket. Nozzle 11 is tubular. The free end thereof, opposite pocket 10, is sealed by a sealing element 13. It is a sleeve which continues along the end portion 12 of the nozzle, and forms an integral part therewith. This sleeve has a compressed end 130 which is for example heat welded.

As shall be seen below, element 13 can be easily detached from the nozzle.

According to an important characteristic of the invention, pump 3 used for dosing and dispensing the product contained in pocket 10, is inserted inside the nozzle 11. This pump 3 has been represented by a dashed line in FIG. 1.

Figure 3:
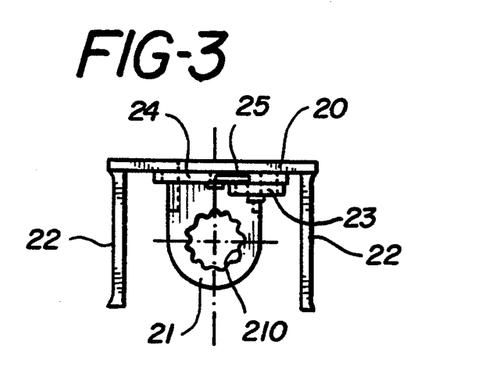

According to another characteristic of the invention, casing 1, as well as the pump and the product contained within this casing, are firmly attached to a rigid support 2. This support is essentially made up of a thin flat rectangular cartridge 20. One of its ends is outfitted with a bracket 21, in this case a little shelf forming a right angle in relation to the plane of cartridge 20. Bracket 21 is crossed by a notched aperture 210 (see FIG. 3). At the level of this bracket, the cartridge presents a cut out 26, having the general shape of a rectangle, extending according to the major axis of the cartridge. At the other end of the cartridge is provided a pair of tabs 22 which also extend at a right angle in relation to the cartridge, on the same side thereof as bracket 21.

At least one of the legs 22 bears on its outer side an informative mark 220-for example the letters "XYZ" inscribed by a jet of visible or luminescent ink.

As can be understood when observing FIG. 1, casing 1 is retained on support 2, on one hand at the level of the nozzle 11, the latter being fit by racheting into aperture 210, on the other hand at the level of pocket 10 which is made to fit between the two legs 22, and consequently maintained centered and immobilized in the opposite direction. The indentations 210 provide good immobilization (in rotation) of nozzle 11 in bracket 21. This aperture penetrates a peripheral groove 100; as can be seen particularly in FIGS. 5 and 6, the outer wall of the nozzle has a truncated cone-like zone 120 bordering groove 100 on the free end side of the nozzle, which facilitates placing the nozzle by racheting into aperture 210, this zone playing the role of leading chamfer. Its locking is ensured by the pump "nozzle".

Cartridge 20 bears a pair of toothed gears 24, 23. Gear 24 having a relatively large diameter, is positioned in line with the cartridge, above cut out 26. It is loose in rotation around a central axis 240. Gear 23, which is smaller, is located above gear 24, and is slightly shifted on one of the sides of the cartridge. It can turn freely around axis 230. Advantageously, the two gears 23, 24 are molded at the same time as the rest of the support, according to a technique known as multiple injection molding.

Figure 2:
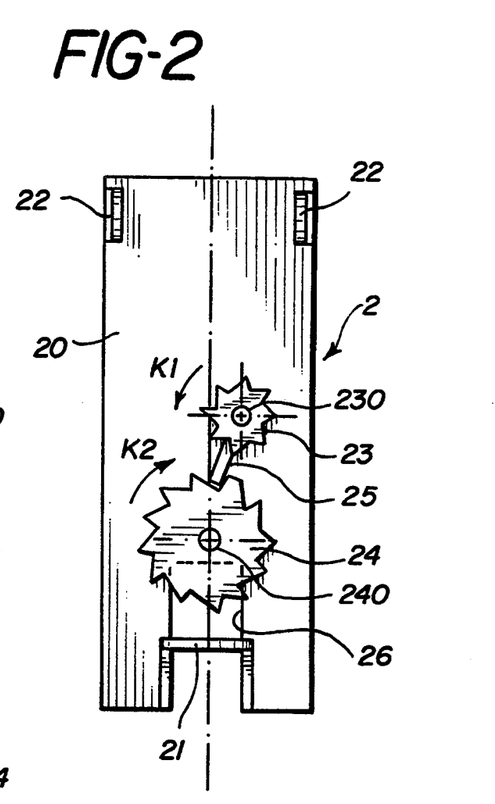
FIGS. 2 and 3 show the rigid support constituent of the vial of FIG. 1, respectively seen from the front and from above.

The planes of gears 24 and 23 are parallel to the plane of cartridge 20. Gear 24 rests against the cartridge, while gear 23 is slightly pushed back therefrom; gear 23 is firmly attached to a driving leg 25 (resulting from molding with the gear) which is resting leg 25 interferes with the teeth of gear 24. The directions of rotation of gears 23 and 24 are symbolized by arrows k1 and, respectively, k2 in FIG. 2. Appropriate anti-return means can be provided, which prevent the movement of the gears in the opposite direction. The forward movement of this device is such that, at each complete turn of gear 23, tab 25 engages via its free end against a tooth of gear 24, to turn the latter by an angle corresponding to the space between two neighboring gears. However, as shall be seen later, particularly in reference to FIG. 21, one (242) of the teeth of gear 24 is larger than and shaped differently from the other teeth (241), in such a way that after a complete turn of gear 24, leg 25 presses against this tooth and blocks itself there, the continuation of movement thus being prohibited.

Figures 4, 5, 6:
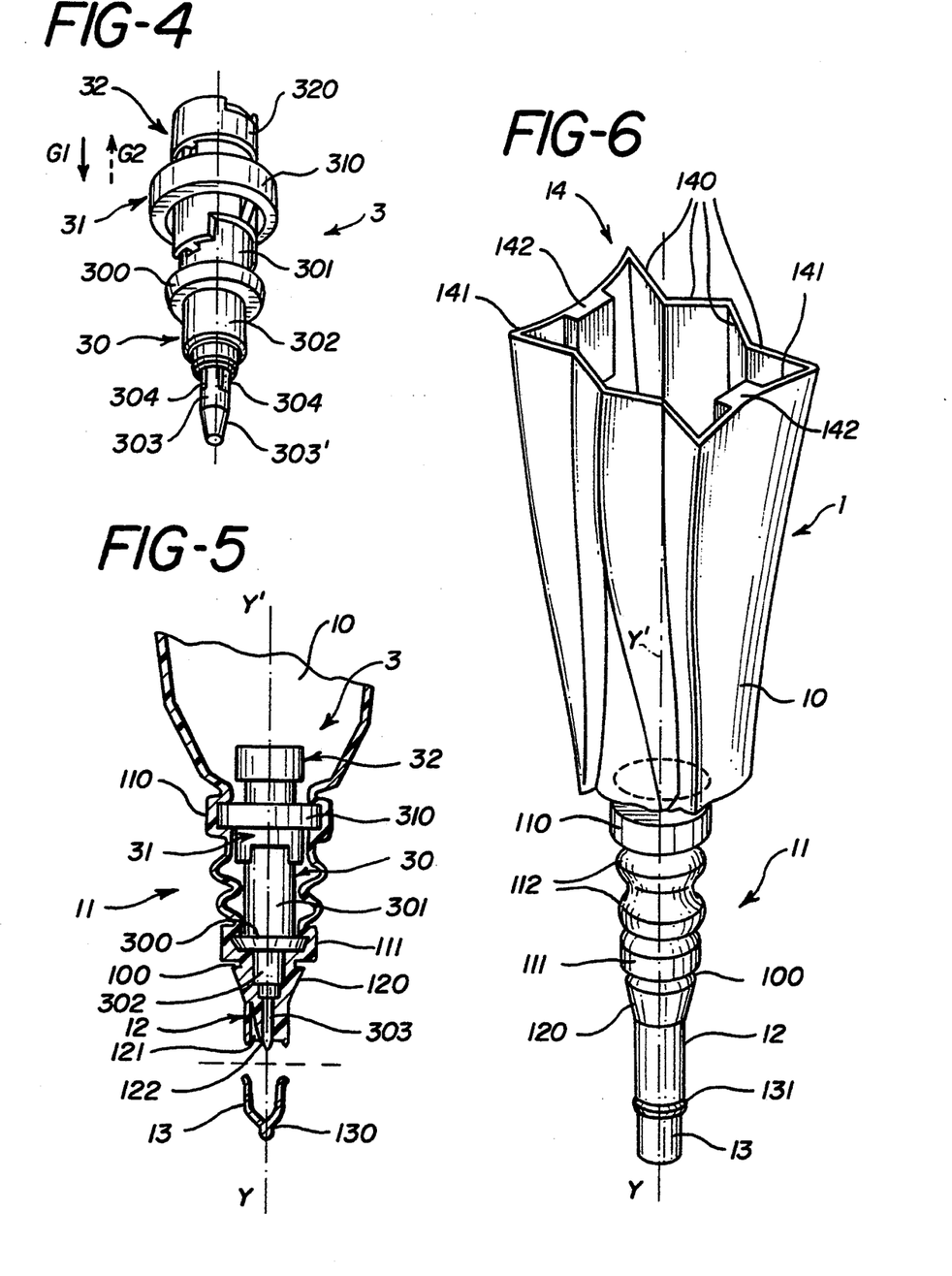

The pump represented in FIG. 4 includes three elements made of molded plastic material, i.e. a fixed body 30, a movable actuating member 31 and a sealing element 32.

Fixed body 30 has a main cylindrical tubular part 301, a truncated cone-like shoulder 300, a cylindrical part 302 and an end part 303 with truncated cone-like tip 303'. Between parts 302 and 303, a step-by-step decrease in diameter is observed. Part 302 is provided with a central bore which comes out from the uphill side (i.e. from the side of pocket 10), inside tubular part 301 and, from the other side (downhill side) by lateral apertures 304 on the outer wall of part 303, slightly before the truncated cone-like tip 303.

The actuating member 31 essentially includes a manuvering base 310 and a central tube (not shown) which penetrates into part 301. Part 31 can nest into part 30; the opposite coupling parts between base 310 and tube 311 are adapted to cross the longitudinal slots provided in part 301.

End element 32 has an inner tubular part (not shown) which can fit without play onto the end of part 301 of fixed body 30. Part 32 also has a bottom and a tubular head 320. After pan 31 is placed on part 30 and coupling (for example by gluing) of part 32 to the end of part 30, the actuating member 31 can travel with a back-and-forward movement, on a limited travel, in relation to the fixed parts 30–32.

The structure of this pump is such that when the actuating member 31 is moved toward tip 303 (symbolized by arrow G1), this will first create an aspiration of the fluid product which surrounds part 31 inside the pump, in a variable-volume chamber. Second, the movement of member 31 in the reverse direction (arrow G2) leads to the expulsion of a calibrated dose—i.e. a well defined volume—of the product outside the chamber. This dose leaves the pump through side openings 304 which are provided in end part 303.

As can be seen more particularly in FIG. 6, aperture 14 of pocket 10 has a contour with the general shape of a rectangle (neighboring that of a square). The large sides thereof show pleats 140 arranged like the bellows of an accordion, while the little sides 141 are not pleated. One understands thus that bottom 14 is sealed by bringing sides 141 together. Note that these latter have extra thicknesses 142 designed to rest one against the other at the end of this coming together, to compensate the superimposed thicknesses of the lateral pleats 140 in the central area of the bottom.

The free end of nozzle 11 has an inner wall shaped for conforming to the outer wall of the pump body 3, except for tubular part 301.

In FIG. 5, the annular part of the wall designed to surround the truncated cone-like shoulder 300 has been designated by reference 111. Near the entrance of pocket 10, the nozzle has an annular part 110 which is adapted to tightly enclose base 310 of actuating member 31 of the pump. Between the annular parts 110 and 111, the wall of the nozzle is thin and presents tipples 112 which make a distortable bellows, capable of being easily compressed or extended according to axis Y-Y'. At the lower end of the nozzle, a cavity 121 is provided which delimits, according to a well determined orientation, a zone 122 easily distortable opposite the end part 303 of the pump body. The role of this zone shall be explained later.

Shall now be explained, referring more particularly to FIGS. 7 through 14, how the manufacturing process for the vial which has just been described is implemented.

Figure 7:
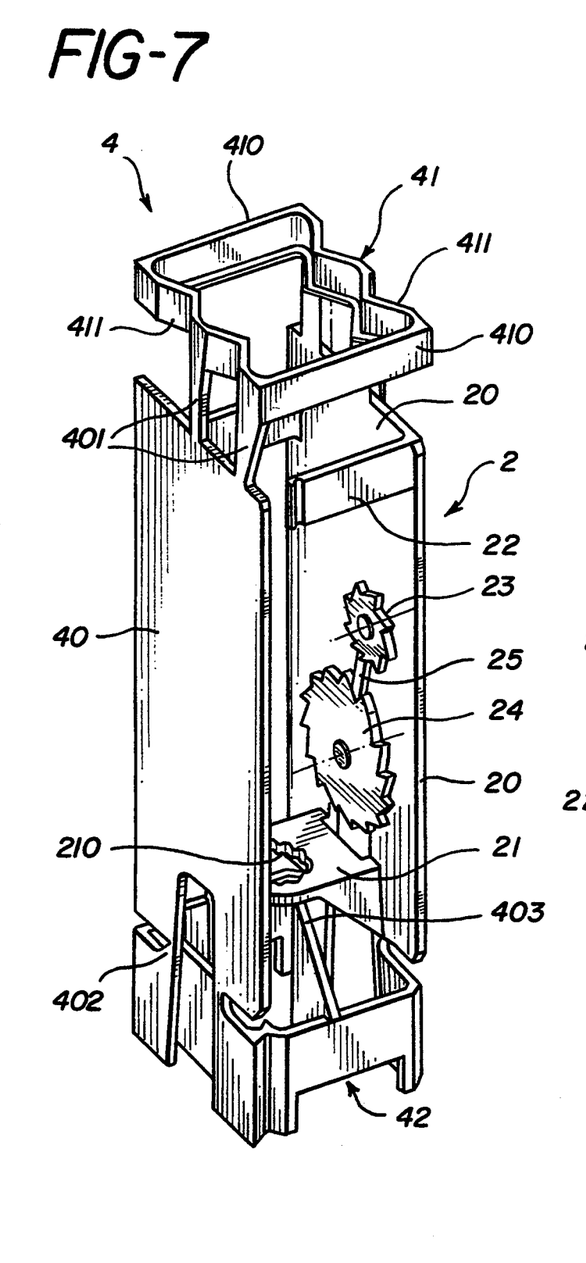
FIG. 7 is a perspective view of the strengthening piece as such when it has just been molded, also at the beginning of the manufacturing process of the vial.
Figure 8:
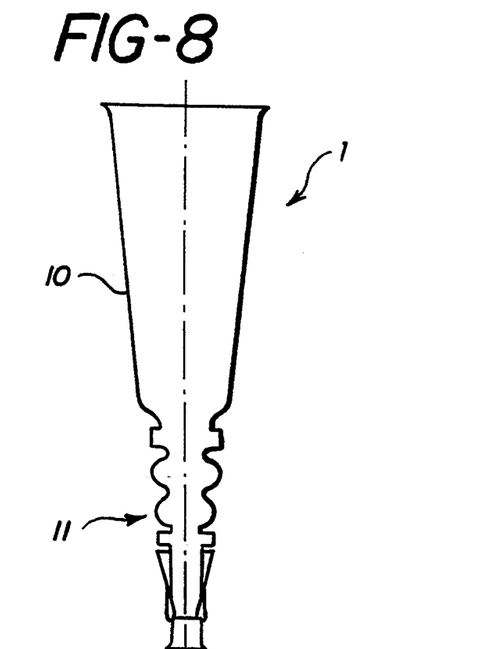
FIG. 8 is a schematic view of the casing, cut by a longitudinal axial plane.
Figure 9:
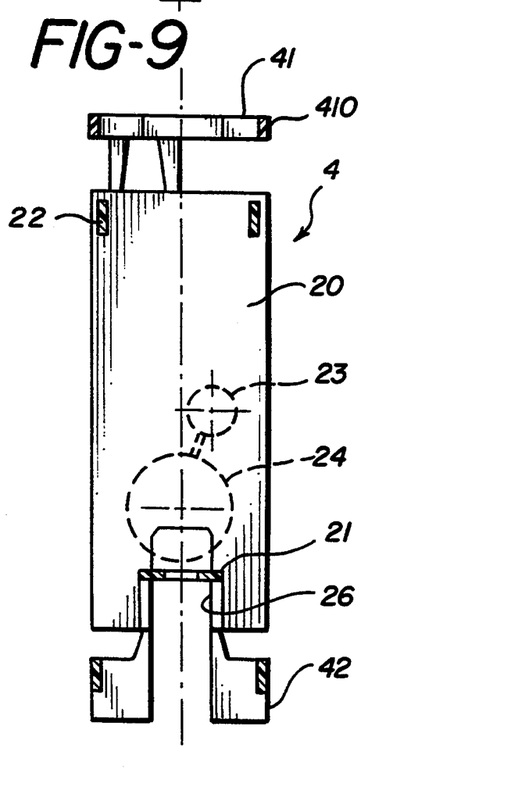
FIG. 9 is a partial cross sectional schematic front view of the strengthening piece, the sectioned surface permitting to see the rigid support in the shape of a cartridge designed to support the casing of FIG. 8.

FIG. 7 represents a strengthening piece made of plastic material, reference 4, which constitutes an important element in the manufacturing process. Part 4 has the general shape of a rectangular parallelepiped delimited by two rectangular cartridges 20, 40, of which one (in this case cartridge 20) is designed to comprise, at the end of manufacture, the above mentioned rigid support. Part 4 has on its upper and lower parts (i.e. on the small sides of parts 20, 40) elements 41, 42 in the shape of a frame. The contour of one of the elements, in this case the upper element 41, corresponds to the contour of the aperture 14 of the pocket.

Element 41 is thus formed of two rigid cartridges 410 opposite each other, coupled by two zigzagging cartridges 411. The element is adapted to receive, through nesting, the upper edge of pocket 10.

Cartridges 20 and 40 are coupled to the two elements 41, 42 by thin tabs 401,402 with low mechanical resistance, easily divisible. The lower element in the shape of a frame 42 is coupled furthermore by fastening tabs 403, also divisible, to bracket 21 of which cartridge 20 is equipped with.

Part 4 is injection molded, all of its constituents, including gears 23, 24, being molded simultaneously.

Casing 1 made of elastomeric material is also obtained by molding.

Figures 10, 11, 12, 13, 16:
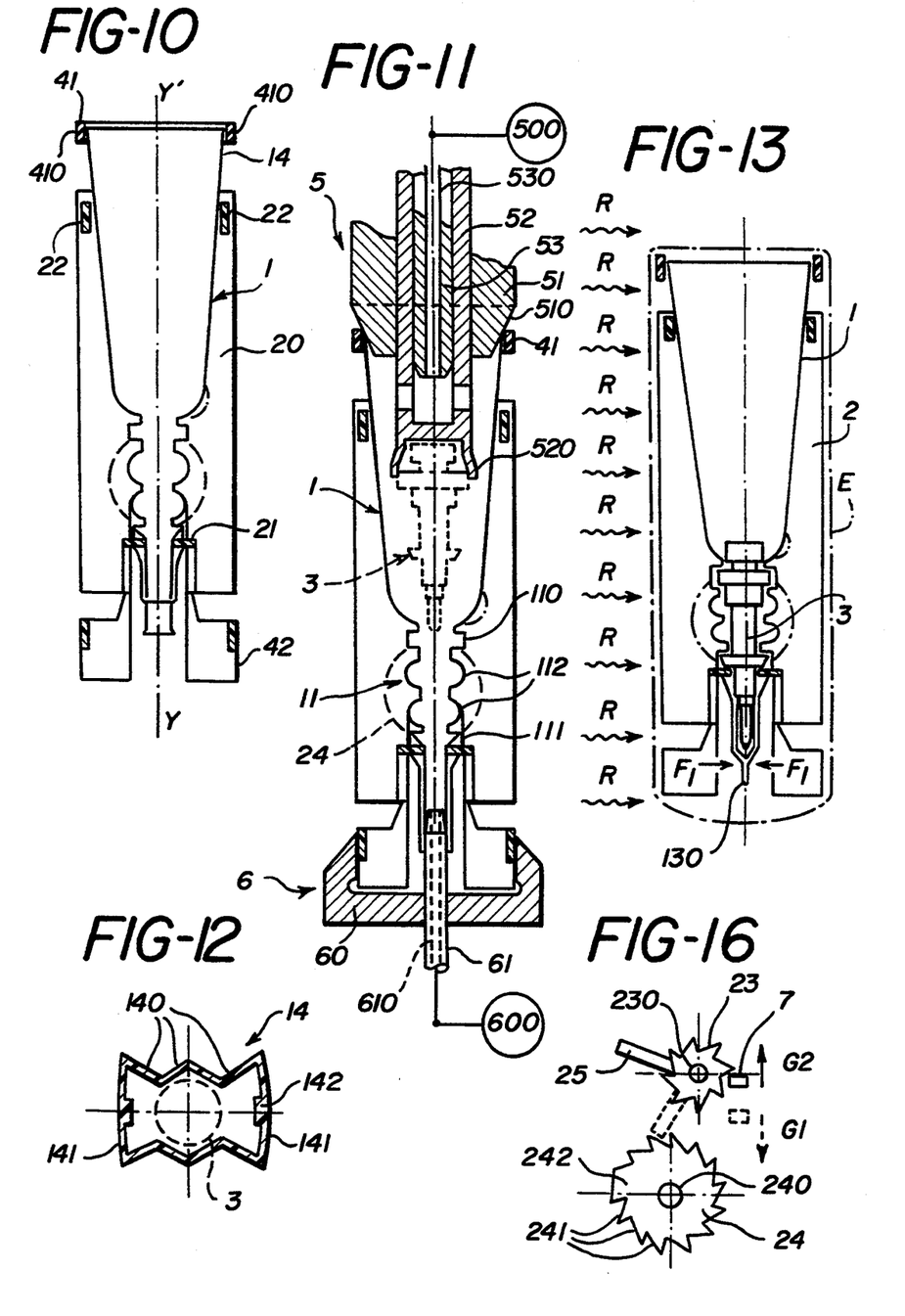
FIG. 10 represents the attachment of the casing of FIG. 9 with the strengthening piece of FIG. 10.
FIG. 11 is intended to illustrate the step of inserting the pump into the nozzle of the casing, as well as the verification tests of the pump.
FIG. 12 is a cross sectional view of the bottom of the pocket constituent of the casing (open side), this view illustrating the manner in which the pump passes when introduced axially into the casing.
FIG. 13 represents the intermediate product comprised of the casing, its support, and the pump, this intermediate product being intended in principle to be transported from the factory to the pharmaceutical or cosmetic laboratory, in which the vial filled.
FIG. 16 is a schematic view of the counting means aiming at illustrating their operation.

The first manufacturing step consists of assembling casing 1 with support 4. For this, it is advantageous to hold the casing on its molding mandrel (not shown); the mandrel being fixed, the frame is displaced so as to nest in the casing.

Of course, the mandrel shape is similar to that of the internal wall of the casing. However, this mandrel is made up of different parts and comprises a retractable (by axial sliding) annular spindle located opposite the nozzle region which supports groove 100. During nesting, the spindle is retracted which makes it possible for the nozzle wall to be momentarily retracted inside so that groove 100 can snap itself on the opening 210 of bracket 21. After the mandrel has been removed, the casing is perfectly maintained inside rigid element 4, at the level of the nozzle and at the level of aperture 14, whose edge presses against element 41 (see FIG. 10). The unit can be thus easily manipulated, particularly for its transport to the following station. Grasping tongs are capable of grasping it without coming into contact with the casing, which is resilient.

The following step will consist of inserting the pump into the casing.

For this, the block comprised of support 4 and pocket 1 is placed in a tool 5, 6, for positioning and maintaining upper and lower elements 41, 42, respectively. The upper tool part 5 includes a ring 51, preferably with chamffered edges 510, adapted to support element 41 by sealingly applying the upper edge of the pocket against stiffening element 41. Inside part 51, a stem 52 of which the end 520 is provided with appropriate means of retaining and centering pump 31, is capable of telescopically sliding. Finally, a mandrel 53, pierced by a central channel 530, is adapted to blow air under pressure, from a source 500 inside the casing. Means 6 provided at the lower end, comprising a member 60 for centering and retaining element 42 and a mandrel 61 capable of sealing the free end of the nozzle. The mandrel 61 is pierced with a central channel 610 connected to a control device 600.

At the beginning of the operation, the control device 600 is piloted so as to seal channel 610. The end of the nozzle is thus sealed. By piloting an appropriate valve, air coming from source 500 is blown under pressure via channel 530, inside casing 1. The latter inflates under the effect of internal pressure, which expands the wall of nozzle 11. At the same time, stem 52 is moved, in the direction of its driving into casing 1, and the pump is inserted into the expanded nozzle. Shoulder 300 of the pump body lodges itself in the annular part 111, while base 310 moves in the annular zone 110. The inside of the casing is then returned to atmospheric pressure, and the nozzle retracts itself to return to its initial shape, trapping the pump.

It should be noted that once the pump is placed in the nozzle, its cylindrical part 302 prevents any collapse toward the inside from the nozzle wall located opposite groove 100. Thus the pump ensures the locking of groove 100 within opening 210, preventing any accidental unfitting.

Following this step, it can be beneficial to take advantage of this tool to carry out pump conformity tests, and to verify that the casing is really sealed, and that the pump body is correctly mounted in the nozzle. For this, employing an appropriate program, air under pressure can be brought to each side of the pump, respectively by channels 530 and 610; flow and pressure measurements may be taken to verify that the pump reacts correctly to the different stresses to which it is subjected. Of course, if these tests conclude that pump and/or casing is non-conform, the entire part is taken off of the assembly line.

It is thus possible, without excessive cost, to carry out a unitary test on the product.

It is also possible, at this step, to provide on at least one of the legs 22 the marking 220 of information, readable or coded, of certain parameters, and in particular the results of the test that was just carried out. For that, the assembly line is equipped with a marking device acting at a right angle.

By observing FIG. 12, it can be easily understood that the special shape of aperture 14 of the casing allows the pump and notably from its base 310 to pass easily therethrough, although the base has a relatively large diameter in relation to the diameter of nozzle 11. Pump 3 passes easily inside the double central pleat of the pocket. Note also that the insertion of the pump takes place in any angular orientation (without indexing in relation to the pocket), which facilitates mounting.

The following step, illustrated in FIG. 13, first consists of closing the end part 13 of the nozzle. This closing takes place simply by heat welding, after crushing symbolized by arrows F1 in FIG. 13.

The manufacturing steps which have just been described are normally carried out not in the laboratory in charge of producing the medicinal or cosmetic product and filling the vial, but though subcontracting in the premises of a manufacturer of plastic material parts. These steps are carried out in a clean room, under laminar flow. In view of transporting them to the laboratory, the intermediate products are going to be temporarily packaged, by being wrapped in a sealed film, this film being represented by a dotted line and referenced as E in FIG. 13.

Once they have arrived at the laboratory, possibly after a more or less long storage time, the products are sterilized inside their casing, by exposing them to the appropriate rays ($\alpha, \beta$ according to each case). This exposure is symbolized by arrows R in FIG. 13.

The following manufacturing steps will be performed in the laboratory in a sterile area, after the packing envelope E is removed.

The first of the following steps consists in filling pocket 10, after upper frame 41 has been torn away. This operation is carried out in a vacuum. Still supported by the stiffening piece 4, the casing is brought into vertical position, aperture 14 turned upwards, at the filling station, which can be of a well-known type. At the level of the filling station, appropriate holding and centering means are provided which enclose lower frame 42 so as to maintain the casing in a fixed and perfectly vertical position. Liquid product 100 is introduced into pocket 10. Upper frame 41 is torn away. Still in a vacuum, and employing the means known per se, the pocket is closed by bringing together sides 141 of opening 14 (arrows F2, FIG. 14). Sealing is accomplished by heat welding; the various wall folds and the extra thicknesses 142 are soldered together to obtain a hermetic sealing. Given that the operation was carded out in a vacuum, there is no air in the pocket once the latter has been sealed.

Figures 14, 15, 17, 17A, 18:
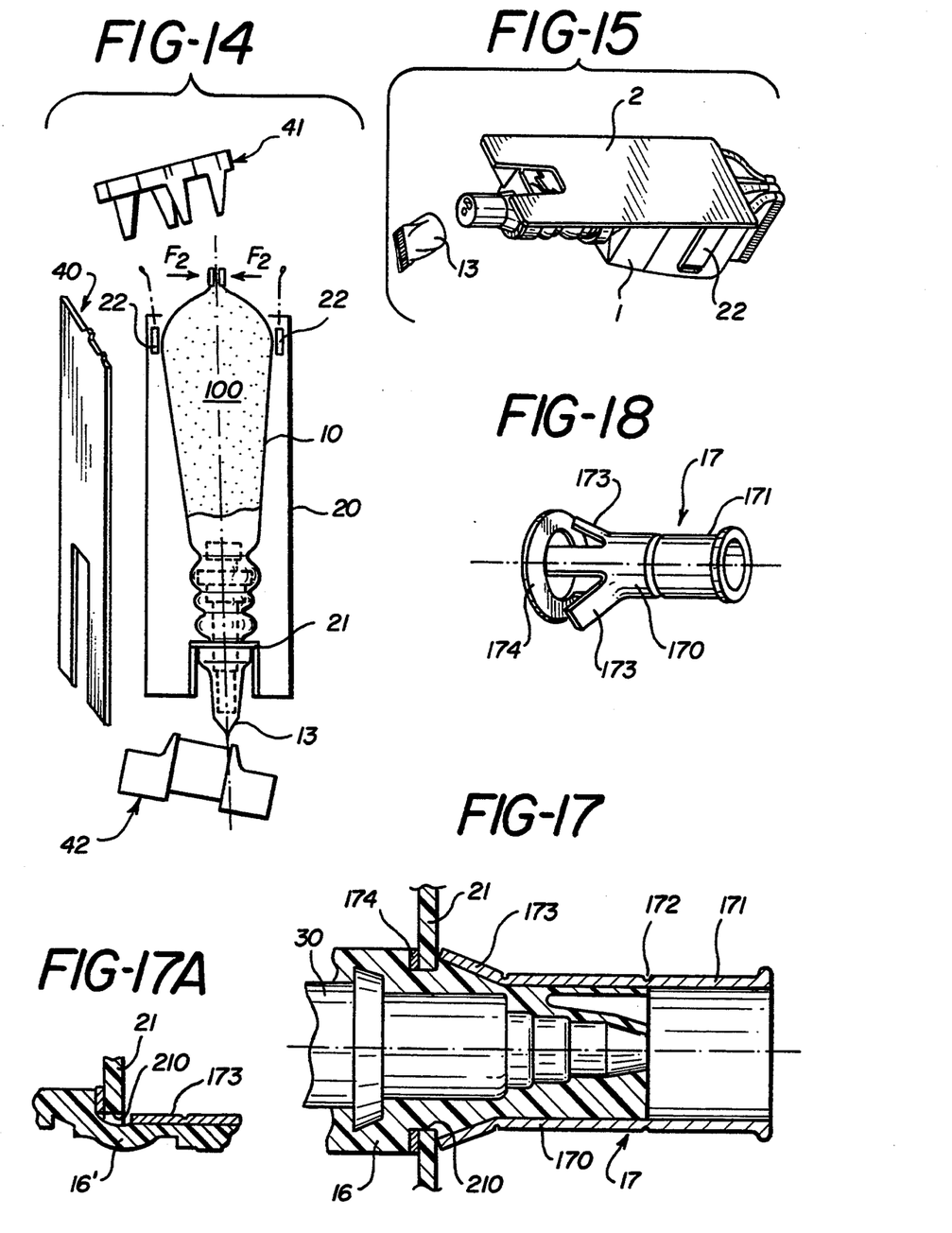
FIG. 14 illustrates the final manufacturing phases, including the filling of the casing, the sealing of the pocket and the pulling off of the superfluous elements of the support.
FIG. 15 is a perspective view of the vial which a user is about to use.
FIG. 17 is a cross sectional view of the extremity of a variation of the vial nozzle, variation in which it a tearaway sealer formed in a tubular piece out of rigid material, distinct from the rest of the nozzle.
FIG. 17A is a partial view corresponding to FIG. 17, showing the deformation of the nozzle when it is placed on the rigid support.
FIG. 18 is a perspective view of this tubular piece (at a smaller scale).

The superfluous elements are then detached from piece 4, i.e. lower frame-shaped part 41 and 42 and cartridge 40.

The unit represented in FIG. 1 is thus obtained, comprised of casing 1, of the rigid cartridge 2 and of the pump 3 contained in the casing.

This unit can be easily and safely handled and stored.

To use the vial, the patient only has to pull off the sealing element 13, as illustrated in FIG. 15. In this respect, note that the sealing sleeve 13 is separated by a weakening groove 131, easily divisible from the rest of the nozzle (see FIG. 6).

The vial is to be used along with a specially adapted distribution device which will not be described herein as it is not within the scope of this invention.

This device comprises a housing for receiving a-vial which is provided with a sliding pushing device which can be actuated by the patient. The pushing device is connected to the annular part 110 of the nozzle and, correlatively, with the base 310 which is used for actuating the pump. Thus, by actuating the pushing device, the patient can first achieve the filling-up of the pump, and second, the distribution of one dose of the product contained in the pocket.

In the case of an eye lotion, the device is provided (as is the case for the above-mentioned device according to EP-A-0 437 953) with an aperture shaped so that it can be applied to the periphery of the eyeball and it is equipped with an eyelid lowering member which is also operated by the plunger and adapted for pushing the eyelid back to the cul-de-sac level during instillation, so that this latter is exposed to the projected drops.

The plunger is firmly attached to a finger which is used for actuating the counter, and which is referenced 7 in picture 16. Finger 17 is configured in such a way that it comes into contact with a tooth of gear 23, during movement of the plunger in a direction, in this case in the G2 direction of its set back position. Appropriate means (such as a rail) retract it during its movement in the opposite direction (G1), in such a way that when it moves forward, it avoids gear 23.

Therefore, each time a dose of eye lotion has been instilled, the plunger goes back to its initial position, finger 7 comes into contact with a tooth of gear 23, thus making this latter move by a fraction of one turn which corresponds to the angular distance between two neighboring teeth. This action is illustrated by arrow G2 in FIG. 16. As mentioned hereinbefore, finger 702 is retracted in the opposite direction so that, during the following forward movement (arrow G1) it does not actuate gear 23.

The number of teeth covering gear 23 is designated by n and the number of normal teeth 241 covering gear 24 by m. As already said above, one of these teeth, referenced as 242 in FIG. 16, has a particular configuration, that of having a size greater than that of teeth 241.

The initial position (just when molded) of leg 25 is such that it drives the first tooth of gear 24, after a complete turn of gear 23, i.e. after n back-and-forward movement(s) of plunger 7. At each one of these complete turns, leg 25 is going to make gear 24 turn a fraction of a turn, corresponding to the angular distance between two teeth 241. After m turns(s) of gear 24, i.e. after $n \times m$ movement(s) of plunger 7, leg 25 is thrust against tooth 242, and movement is thus blocked. Of course, the number $n \times m$ is chosen so that practically all the liquid which was contained in the vial has been at this moment delivered, the small amount left over leading to inaccuracy regarding dosage and dispensing.

Thus, relating to an eye lotion that generally must be dispensed morning and evening in each eye, it is possible to provide a vial containing a volume of product for thirty days therein, with the result that one will choose $n \times m = 2 \times 2 \times 30 = 120$. Thus, it is possible for example to provide a gear 23 with eight teeth and a gear 24 with fifteen teeth (plus a special blocking tooth).

It is important to note that during dispensing of the product, air cannot penetrate into casing 1. In fact, as soon as a stream of liquid has been expelled at the end of the nozzle, the distortable zone 122 intimately applies itself, because of its elasticity, against the truncated cone-like end 303 of the pump body. As can be seen more particularly in FIG. 19, a series of apertures 124 can be advantageously provided at the end of the nozzle to increase the flexibility thereof and to further improve its adaptation against the pump body.

Since the entry of air is not possible, pocket 10 distorts itself by contracting onto itself, which results from the thinness and the flexibility of its wall.

Figure 19:
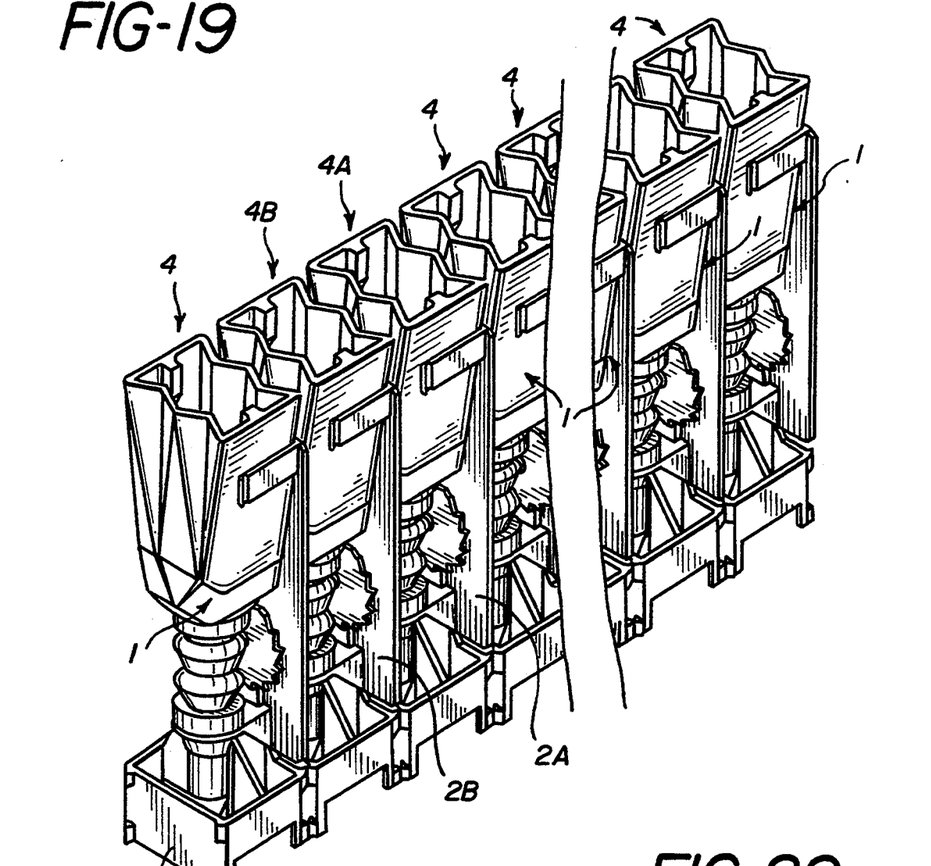
FIG. 19 is a perspective view representing an intermediate product (during manufacture), formed of a set of juxtaposed vials.

FIG. 19 represents a set of 4 juxtaposed pieces, which were molded simultaneously. Upper elements 41 equipping this set, are supposed to have already been torn off. Each piece 4A making up this set is similar to the strengthening piece 4 described above. However, the two cartridges delimiting the rectangular parallelepiped of piece 4A, consist in its own rigid support 2A for one of them, and in rigid support 2B of an adjacent piece 4B for the other.

Once all the casings have been filled and sealed, elements 42 are pulled off and the vials are separated from each other before they are sold.

It is important to note that, given that the counting means 23, 24, 25 are firmly attached to the vial, and not to the device that delivers the product, the counting means do not reset to zero if the vial is momentarily taken out of the device. To these means of counting can be advantageously added means of supplementary information for the user. Thus, for example, gear 24 can be provided with a color mark or a number which becomes visible through an appropriate window of the delivering device when the number of doses delivered reaches the maximum number allowed.

Figure 20:
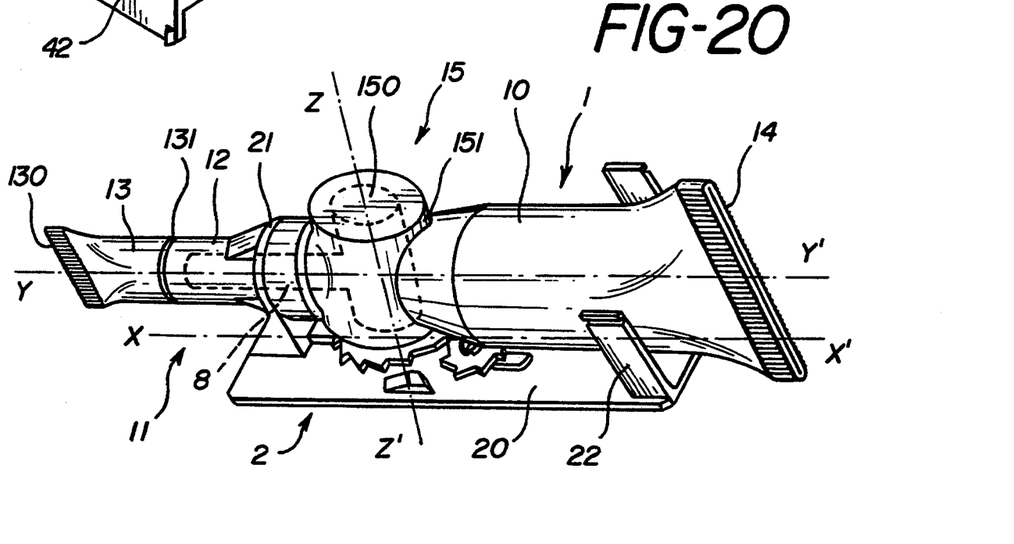
FIG. 20 is a perspective view of a second embodiment of the vial according to this invention.

The vial which is the object of the embodiment illustrated in FIG. 20 has the same general type as the one previously described. This is why the same reference numbers have been used to designate the elements identical or analogous to those of the first embodiment.

The vial includes a casing 1, composed essentially of a flexible pocket 10, of a nozzle 11, the whole unit being coupled to a rigid cartridge 20. The nozzle 11 is inserted into an aperture of bracket 21. Pocket 10 has an almost circular section. It is maintained centered on cartridge 20 by maintaining legs 22.

Figures 21, 22:
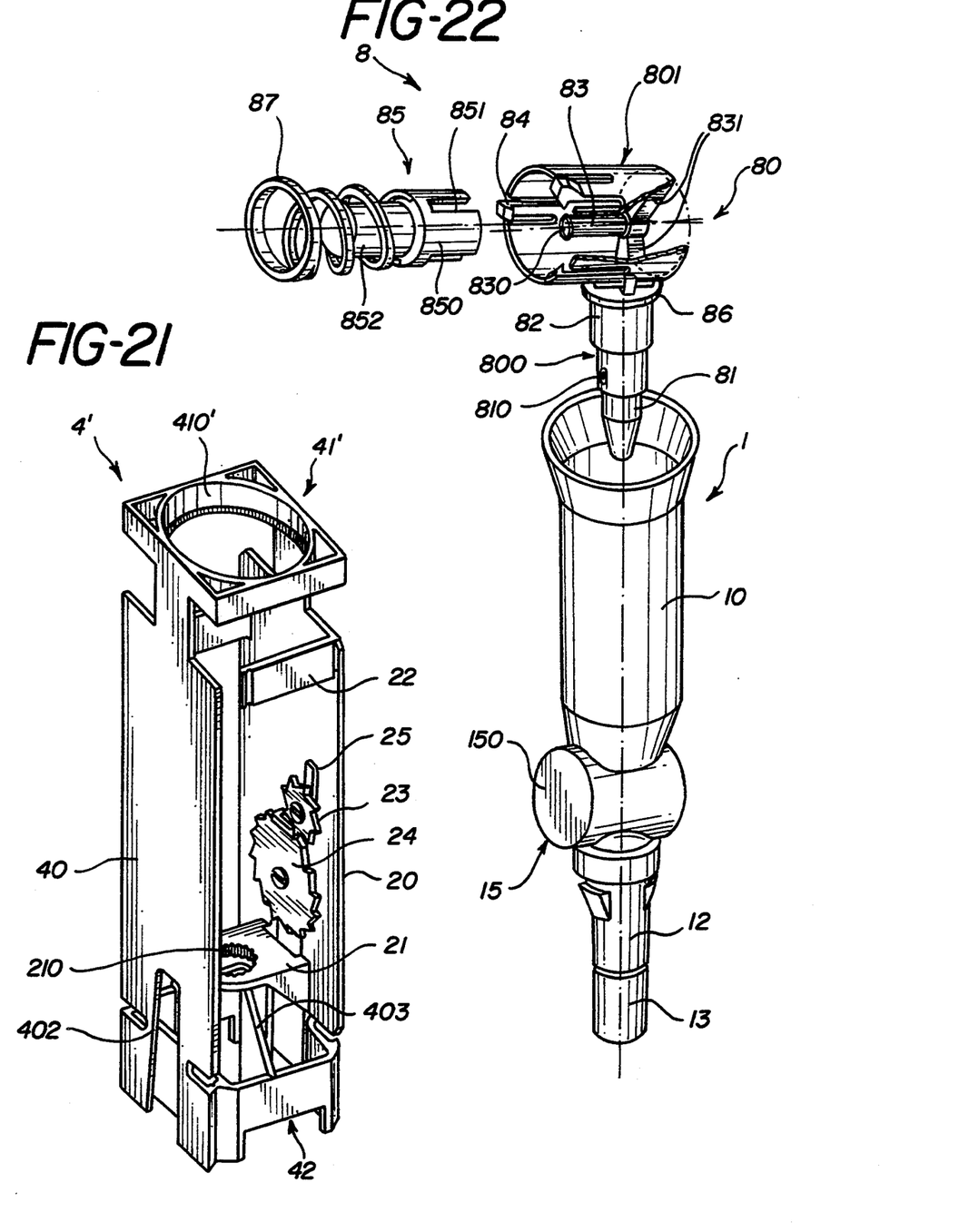
FIG. 21 is a perspective view (id. as FIG. 7) of the strengthening piece used for the manufacturing of vial of FIG. 20.
FIG. 22 is an exploded perspective view, illustrating the pump and the flexible pocket which make up said vial, before they are assembled.

Strengthening piece 4' used for the manufacturing of this vial, represented in FIG. 21, is similar to that represented in FIG. 7, in relation with the first manufacturing process.

Its only difference lies in the upper pull-off element 41'' which is frame-shaped and whose inner wall 410'' is circular so that it can match the shape of the opening of vial 10.

This embodiment distinguishes itself essentially from the previous one by the configuration of the pump 8 with which it is equipped. As can be seen more particularly in FIG. 22, body 80 of this pump presents two pans forming a right angle, which gives it the general look of a pipe. Reference 800 has been used to designate one of these parts—which corresponds to the tube of the pipe—and reference 801 has been used to designate the other part—which corresponds to the bowl of the pipe.

Figure 23:
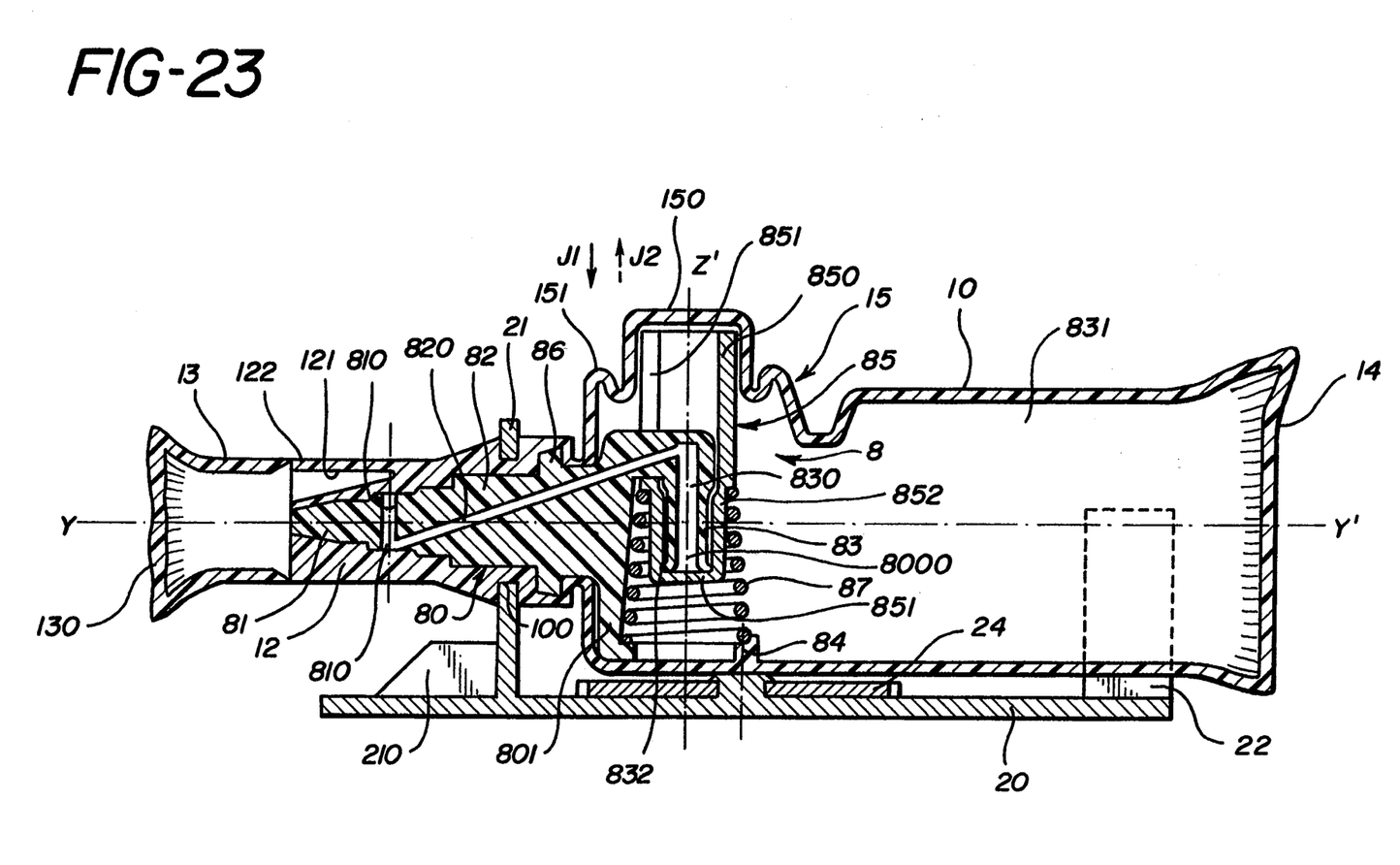
FIG. 23 is a longitudinal sectional view of the vial of FIG. 20.

Part 800 has the shape of a revolution, with axis Y-Y'' corresponding to the axis of the nozzle. This part 800 is inserted into the nozzle, in the same manner as the pump body 30 of the first embodiment. It has thus a truncated cone-like shoulder 86 capable of elastically racheting itself into the wall of the nozzle. From this shoulder to the free end of part 800, one finds a cylindrical part 82, of which the diameter decreases step-by-step until the truncated cone-like tip 81. Part 801 has a generally tubular outer wall, with axis Z-Z'', which is coupled by radial blades 83 1 to a central tube 83. The latter has an annular sealing lip 830 at its free end. Part 800 is pierced with a channel 820 which, on the uphill side, comes out inside tube 830 and on the downhill side, comes out outwardly by lateral apertures 810, a little before the tip 81. The pump furthermore includes a generally cylindrical part 85, including a closed end and an open end. The closed end consists of a socket 852 which is provided with a flat bottom 851, adapting to the tubular part 83 like a cylinder on a piston. The part of the member 85 located on the open side is a sleeve coaxial with part 852, presenting longitudinal slits 851 permitting its engagement on pump body 80. Part 801 of the pump body has elements 84 serving as a stop for a compression spring 87, located inside pocket 10, and pulling member 85 to bring it into contact with the wall of pocket 10 in a zone 15 which is distortable, for instance in the shape of a bellows. Spring 87 can be made of plastic material and can be molded along with pulling member 85. In FIG. 23, reference 150 has been used to designate the Circular region of the pocket against which the front side of member 85 rests, and reference 151 has been used to designate a pleat in the bellows 15. This latter can be omitted due to the resilience of the wall of pocket 10 and because its ability to be distorted is only required over a very short strike (in the range of a few millimeters).

The simple observation of FIG. 23, one can understand that by pressing on zone 150 according to the Z-Z'axis, member 85 is made to go down inside pocket 10 while compressing spring 87. This increases the volume in chamber 8000 comprising bore 830 and the space at the bottom of socket 852.

The device used to deliver the product contained in this vial, (not shown) includes a housing in which the vial is located and positioned. Means for retaining and centering of cartridge 20 (not shown) are provided in the housing.

This device includes actuating means which can be directly operated by the patient and configured to create or authorize:

in the first place, the lowering of the pulling member 85 (arrow J1, FIG. 23); this achieves the aspiration of the product contained in pocket 10 in the chamber 8000;

second, the upward movement of pulling member 85 via the action of spring 87 (arrow J2, FIG. 23); this achieves the back flow of one dose of the product outside the chamber 8000 and its expulsion at the level of the nozzle end, via channel 820 and openings 810. As in a first embodiment, the distribution of the product is carried out as an oriented jet of drops, because of the presence of cavity 121 of the nozzle and because of the cone shape of the end tip 81 of the pump body.

In the variation of FIGS. 17 and 18, the end of the nozzle of the casing is formed of two different pieces. Wall 16 of the nozzle which surrounds the end of the pump body 30 is made of elastomeric material, forming an integral part with the rest of the casing. On this end is molded on a part 17 having a general tubular shape, made of a relatively rigid plastic material. Part 17 is made up of a first part 170 serving to attach the nozzle in the hole 210 of bracket 21 and of a second end part 171 serving as a sealer. These two parts are separated by a least resistant (divisible) groove 172. Part 170 presents a flange 174 designed to press against one of the two sides of bracket 21, while pressing on the other side is obtained by two tabs 173 turned outwardly, and whose elasticity permits the racheting in aperture 210. The sealing of pan 171 is made by crushing and heat welding.

FIG. 17A illustrates the placing of nozzle end pan in the aperture 210 (pump not inserted yet). Tabs 173 are folded in the direction of the material, parallel to the axis of the nozzle, whereas the wall made of elastomeric material is also distorted insidely at the level of 16" which permits the introduction of the whole in aperture 210.

Molding rigid element 17 on the end 16 of the nozzle, can be accomplished through a technique known as sequencing molding. Given its rigidity, sealing element 171 can be tom off more easily than if it were flexible, like the rest of the nozzle, which improves the convenience of use of the vial.

This construction can be achieved for the first as well as for the second embodiment.

The dimensions of the vial, the capacity of the pocket, and the flow characteristics of the pump shall of course be chosen as a function of the application.

What is claimed is:

1. A packaging vial for dispensing in calibrated successive doses a liquid medicinal product comprising:
   a flexible casing containing the product, being free from air, comprising a pocket having a thin and deformable wall, and having a tubular nozzle connected to said casing for discharging the product;
   a pump including a fixed body inserted into said nozzle and a moveable actuating member disposed inside said casing and displaced through said thin and deformable wall of said casing, said fixed body including a chamber wherein movement of said actuating member in a first direction draws the product into said chamber while movement of said actuating member in an opposite second direction discharges a calibrated dose of the product from the chamber; and
   a rigid support coupled to said casing and having a counting means for counting the number of doses of the product dispensed, said counting means comprising a first freely rotating toothed gear and a second freely rotating toothed gear, said first gear having an actuating leg connecting said first gear to said second gear whereby actuating said actuating member causes the product dose to be dispensed and also turns said first gear a fraction of a turn and whereby upon a complete revolution of said first gear said second gear turns a fraction of a turn thereby counting the number of product doses dispensed.

2. The packaging vial as defined in claim 1 wherein one of said teeth of said second gear is shaped to prohibit rotation of said second gear after said second gear has rotated one complete revolution.

3. The packaging vial as defined in claim 2 wherein said fixed body of said pump further comprises:
   a channel extending through said fixed body connecting said casing to said nozzle, said channel terminating at an outlet portion of said fixed body and at an outlet portion of said nozzle, said nozzle having a deformable inner wall intimately lying against an outer wall of the outlet portion of said fixed body thereby sealing the outlet portion of said fixed body wherein the pressure of the product dose deforms the deformable zone to unseal the outlet portion of said fixed body to effect discharge of the product dose through said nozzle.

4. The packaging vial as defined in claim 3 wherein the nozzle further comprises:
   a relatively firm outer wall surrounding said deformable inner wall and said fixed body thereby causing the ejection of the product dose over a predetermined space.

5. The packaging vial as defined in claim 4 wherein the deformable inner wall is formed by a cavity cut in the outer wall of the nozzle.

* * * * *